United States Patent [19]   [11]  4,238,220
Carlson                                  [45]  Dec. 9, 1980

[54] 1-ARYL-5-CARBOXY-2-PYRIDONES AND DERIVATIVES THEREOF

[75] Inventor: Glenn R. Carlson, North Wales, Pa.

[73] Assignee: Rohm and Haas Company, Philadelphia, Pa.

[21] Appl. No.: 57,854

[22] Filed: Jul. 16, 1979

Related U.S. Application Data

[63] Continuation-in-part of Ser. No. 816,051, Jul. 15, 1977, abandoned.

[51] Int. Cl.³ .................. A01N 9/22; C07D 213/55
[52] U.S. Cl. ........................................ 71/94; 546/298
[58] Field of Search ............................ 546/298; 71/94

[56] References Cited

U.S. PATENT DOCUMENTS

| 2,947,754 | 8/1960 | Scudi | 546/298 |
| 3,503,986 | 3/1970 | Seidel et al. | 546/298 |
| 3,576,814 | 4/1971 | Seidel et al. | 546/298 |
| 3,711,488 | 1/1973 | Bayer et al. | 546/298 |
| 4,028,084 | 6/1960 | McNulty et al. | 71/94 |
| 4,051,142 | 9/1977 | Carlson | 546/288 |

OTHER PUBLICATIONS

Prey et al., Monatsh, vol. 91, pp. 774–793 (1960).
Prey et al., Chemical Abstracts, vol. 56, Col. 15469, (1962).
Eiden et al., Chemical Abstracts, vol. 78, 136078-z (1973).
Ried et al., Chemical Abstracts, vol. 78, 15,976g (1973).
Chemical Abstracts, 7th Collective Index, (vols. 56–65) p.15,233-s (1970).
Rubtsov, Chemical Abstracts, vol. 34, Col. 2845, (1940).
Beilstein's Handbuch der Organischen Chemie, vol. 22, 4th Edition, Springer Pub. Berlin Germany (1935).

*Primary Examiner*—Alan L. Rotman

[57] ABSTRACT

Compounds of the formula wherein
$R^1$ is alkyl,
$R^2$ is carboxy, carboxylate, or carbalkoxy
$R^3$ is hydrogen or alkyl,
$R^4$ is hydrogen, alkyl, or halogen and
$R^5$ is optionally substituted aryl, are active as plant growth regulators, and particularly as chemical gametocides.

10 Claims, No Drawings

1-ARYL-5-CARBOXY-2-PYRIDONES AND DERIVATIVES THEREOF

This application is a continuation-in-part application of U.S. Ser. No. 816,051 filed July 15, 1977, now abandoned.

This invention relates to novel compounds which show activity as plant growth regulators, particularly as chemical gametocides, to growth regulant compositions which comprise these compounds, and to methods of regulating the growth of plants with these compounds and compositions.

A new class of compounds has now been found which can be used as plant growth regulators, and particularly as chemical gametocides in cereal grains. U.S. application Ser. No. 826,920 filed Aug. 22, 1977 by Gerard Sutra discloses the use of these compounds for ergot production, the data for which is incorporated herein by reference. The compounds of the invention are 2-pyridones having the formula

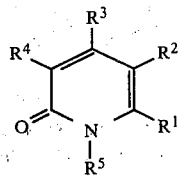

wherein $R^1$ is an alkyl group, preferably having up to 4 carbon atoms, $R^2$ is a carboxy group (—COOH) or an agronomically-acceptable salt thereof, or a carbalkoxy group (—COOR, wherein R is an alkyl group, preferably having up to 12 carbon atoms, most preferably up to 4 carbon atoms), $R^3$ is a hydrogen atom or an alkyl group, preferably having up to 4 carbon atoms, $R^4$ is a hydrogen atom, an alkyl group, preferably having up to 4 carbon atoms, or a halogen atom, preferably a bromine or a chlorine atom, and $R^5$ is an optionally substituted aryl group, preferably a phenyl group, a substituted phenyl group, a naphthyl group, or a substituted naphthyl group.

In a preferred embodiment of the invention, $R^1$ is a methyl group, $R^2$ is a carboxy group or a salt thereof, $R^3$ is a hydrogen atom or a methyl group, $R^4$ is a hydrogen atom or a halogen atom, and $R^5$ is a substituted phenyl group.

When $R^2$ is a salt of a carboxy group, an alkali metal, alkaline earth metal, or transition metal can provide the cation. The cation can also be ammonium or substituted ammonium. Representative metal salt cations include alkali metal cations, such as sodium, potassium, lithium, or the like, alkaline earth metal cations, such as calcium, magnesium, barium, strontium, or the like, or heavy metal cations, such as zinc, manganese, cupric, cuprous, ferric, ferrous, titanium, aluminum, or the like. Among the ammonium salts are those in which the ammonium cation has the formula $NZ^1Z^2Z^3Z^4$, wherein each of $Z^1$, $Z^2$, $Z^3$, and $Z^4$ is individually a hydrogen atom, a hydroxy group, a $(C_1-C_4)$alkoxy group, a $(C_1-C_{20})$alkyl group, a $(C_3-C_8)$alkenyl group, a $(C_3-C_8)$alkynyl group, a $(C_2-C_8)$hydroxyalkyl group, a $(C_2-C_8)$alkoxyalkyl group, a $(C_2-C_6)$aminoalkyl group, a $(C_2-C_6)$haloalkyl group, a substituted or unsubstituted phenyl group, a substituted or unsubstituted phenylalkyl group, having up to 4 carbon atoms in the alkyl moiety, an amino or alkyl-substituted amino group, or any two of $Z^1$, $Z^2$, $Z^3$, or $Z^4$ can be taken together to form with the nitrogen atom a 5- or 6-member heterocyclic ring, optionally having up to one additional hetero oxygen, nitrogen, or sulfur atom in the ring, and preferably saturated, such as a piperidine, morpholine, pyrrolidine, or piperazine ring, or the like, or any three of $Z^1$, $Z^2$, $Z^3$, or $Z^4$ can be taken together to form with the nitrogen atom a 5- or 6-member aromatic heterocyclic ring, such as pyrazole or pyridine ring. When the ammonium group contains a substituted alkyl, substituted phenyl or substituted phenylalkyl group, the substituents will generally be selected from halogen atoms, $(C_1-C_8)$alkyl groups, $(C_1-C_4)$alkoxy groups, a hydroxy group, nitro groups, trifluoromethyl groups, cyano groups, amino groups, $(C_1-C_4)$alkylthio groups, and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, diallylammonium, pyrazolium, propargylammonium, dimethylhydrazinium, hydroxyammonium, methoxyammonium, dodecylammonium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like.

Among the substituents which $R^5$ can contain are alkyl groups, preferably having up to 4 carbon atoms, aryl groups, preferably phenyl or substituted phenyl groups, alkoxy groups, preferably having up to 4 carbon atoms, phenoxy or substituted phenoxy groups, halogen atoms, such as fluorine, chlorine, bromine, and the iodine atoms, nitro groups, perhaloalkyl groups, such as trifluoromethyl groups, alkoxyalkyl groups, preferably having up to 6 carbon atoms, alkoxyalkoxy groups, preferably having up to 6 carbon atoms, amino groups, alkyl or dialkyl amino groups, preferably having up to 4 carbon atoms in each alkyl substituent, cyano groups, carboxy groups, carbalkoxy groups, preferably having up to 4 carbon atoms in the alkoxy moiety, carbamoyl groups, alkyl or dialkyl carbamoyl groups, preferably having up to 4 carbon atoms in each alkyl substituent, sulfo groups, sulfonamido groups, alkylcarbonyl or carboxyalkyl groups, preferably having up to 4 carbon atoms in the alkyl moiety, alkanoyloxy groups, preferably having up to 4 carbon atoms, haloalkyl groups, alkanoylamido groups, preferably having up to 4 carbon atoms, alkylthio groups, preferably having up to 4 carbon atoms, alkylsulfinyl groups, preferably having up to 4 carbon atoms, alkylsulfonyl groups, preferably having up to 4 carbon atoms, and the like. Generally, $R^5$ will have up to two substituents. The most preferred substituents are halogen atoms, preferably with at least one in the 4-position, $(C_1-C_4)$alkyl groups, preferably 4-methyl, $(C_1-C_4)$alkoxy groups, preferably 4-methoxy, trifluoromethyl groups, preferably 4-trifluoromethyl, and nitro groups, preferably 4-nitro.

Typical compounds within the scope of this invention include:

N-(4-chlorophenyl)-5-carboxy-4,6-dimethylpyrid-2-one
N-(3-chlorophenyl)-5-carboxy-4,6-dimethylpyrid-2-one
N-(4-bromophenyl)-5-carboxy-4,6-dimethylpyrid-2-one
N-(2-chlorophenyl)-5-carboxy-4,6-dimethylpyrid-2-one
N-(4-iodophenyl)-5-carboxy-4,6-dimethylpyrid-2-one
N-(2-fluorophenyl)-5-carboxy-4,6-dimethylpyrid-2-one
N-(4-trifluoromethylphenyl)-5-carboxy-4,6-dimethylpyrid-2-one
N-(4-methoxyphenyl)-5-carboxy-4,6-dimethylpyrid-2-one
N-(3-nitrophenyl)-5-carboxy-4,6-dimethylpyrid-2-one
N-(4-cyanophenyl)-5-carboxy-4,6-dimethylpyrid-2-one
N-(4-chlorophenyl)-5-carboxy-6-methylpyrid-2-one
N-(4-nitrophenyl)-5-carboxy-6-methylpyrid-2-one
N-(4-cyanophenyl)-5-carboxy-4,6-dimethylpyrid-2-one
N-(3-ethoxyphenyl)-5-carboxy-6-methylpyrid-2-one
N-(4-methylphenyl)-5-carboxy-6-methylpyrid-2-one
N-(3,4-dichlorophenyl)-5-carboxy-6-methylpyrid-2-one
N-(4-methyl-3-chlorophenyl)-5-carboxy-6-methylpyrid-2-one
N-(4-chlorophenyl)-5-carboxy-3,4,6-trimethylpyrid-2-one
N-(4-bromophenyl)-5-carboxy-4,6-diethylpyrid-2-one
N-(4-chlorophenyl)-5-carboxy-4,6-diethylpyrid-2-one
N-(4-bromophenyl)-5-carboxy-4,6-dipropylpyrid-2-one
N-(4-chlorophenyl)-5-carboxy-4-ethyl-6-methylpyrid-2-one
N-(4-trifluoromethylphenyl)-5-carboxy-6-ethyl-4-methylpyrid-2-one
N-(4-chlorophenyl)-5-carboxy-6-ethylpyrid-2-one
N-(4-bromophenyl)-5-carboxy-6-propylpyrid-2-one
N-(4-chlorophenyl)-5-carboxy-3,6-dimethylpyrid-2-one
N-(4-trifluoromethylphenyl)-5-carboxy-3,6-dimethylpyrid-2-one
N-((4-bromophenyl)-5-carboxy-6-methylpyrid-2-one
N-(3,4-dichlorophenyl)-5-carboxy-4,6-dimethylpyrid-2-one
N-(2-chloro-4-methylphenyl)-5-carboxy-4,6-dimethylpyrid-2-one
3-bromo-N-(4-chlorophenyl)-5-carboxy-4,6-dimethylpyrid-2-one
3-bromo-N-(4-fluorophenyl)-5-carboxy-4,6-dimethylpyrid-2-one
3-chloro-N-(2,4-dichlorophenyl)-5-carboxy-4,6-dimethylpyrid-2-one
3-fluoro-N-(3-chlorophenyl)-5-carboxy-4,6-dimethylpyrid-2-one
3-bromo-N-(4-trifluoromethylphenyl)-5-carboxy-6-methylpyrid-2-one
and agronomically-acceptable salts of the above acids,
N-(4-chlorophenyl)-5-carbomethoxy-4,6-dimethylpyrid-2-one
N-(4-fluorophenyl)-5-carboethoxy-4,6-dimethylpyrid-2-one
N-(3-methylphenyl)-5-carbobutoxy-4,6-dimethylpyrid-2-one
N-(3,4-dichlorophenyl)-5-carboethoxy-6-methylpyrid-2-one
N-phenyl-5-carbmethoxy-6-methylpyrid-2-one
and the like.

The compounds of the invention can be prepared by several convenient preparative routes. In the first method, an acid chloride of the formula

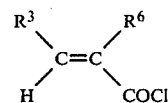

(II)

wherein $R^6$ is a hydrogen atom or an alkyl group, and $R^3$ is as defined above, is condensed with an enamine of the formula

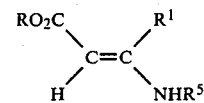

(III)

wherein R, $R^1$, and $R^5$ are as defined above, to yield a dihydropyridone of the formula

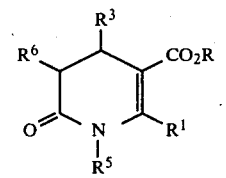

wherein R, $R^1$, $R^3$, $R^5$, and $R^6$ are as defined above. This reaction is generally carried out in an inert solvent, such as ethyl ether, methylene chloride, benzene, toluene, or the like, at a temperature of about 0° to about 100° C. The dihydropyridone is then dehydrogenated in the presence of a dehydrogenating agent, such as 2,3-dichloro-5,6-dicyano-1,4-benzoquinone or similar quinone, palladium on charcoal, N-bromosuccinimide, or the like, in an inert solvent, such as benzene, xylene, chlorobenzene, or the like, generally at a temperature of about 50° C. to about 250° C. to form a pyridone of the formula

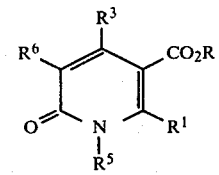

wherein R, $R^1$, $R^3$, $R^5$, and $R^6$ are as defined above. The ester can then be converted to the corresponding acid or salt by a conventional hydrolysis, such as sodium hydroxide, potassium, hydroxide or the like, at ambient or elevated temperature of up to about 100° C.

In a second preparative route to compounds of the invention, a pyrone of the formula

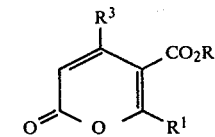

wherein R, $R^1$, and $R^3$ are as defined above, is reacted with an amine of the formula $NH_2-R^5$  (VII)

wherein $R^5$ is as defined above, in the presence of an acid catalyst, such as p-toluenesulfonic acid, methanesulfonic acid, hydrochloric acid, sulfuric acid, or the like, in an inert solvent such as chlorobenzene, toluene, xylene, cumene, or the like, or using 50% aqueous acetic acid as the reaction medium, to form a pyridone of the formula

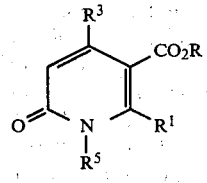

wherein R, $R^1$, $R^3$, and $R^5$ are as defined above. This reaction is generally carried out at a temperature of about 50° C. to about 250° C. The free acid and its salts can then be prepared by conventional techniques.

The compounds of the invention in which $R^4$ is a halogen atom can be prepared by reacting the corresponding 4-pyridones in which $R^4$ is a hydrogen atom with one equivalent of a halogenating agent such as bromine, chlorine, sulfuryl bromide, sulfuryl chloride, or the like in a suitable inert solvent such as ethylene dichloride, methanol, or the like, generally at a temperature of about 0° to about 100° C.

The following examples will further illustrate the compounds of the invention and their preparation, but are not intended to limit the invention in any way. All temperatures are in degrees Celsius and parts and percentages are by weight, unless otherwise indicated. Specific illustrative preparations of the compounds of Examples 1, 19, 25, 28, and 30 are provided. Table I lists typical compounds of the invention and their melting points and elemental analysis.

TABLE I

| Ex. No. | X | Y | R | MP | C | H | N | X |
|---|---|---|---|---|---|---|---|---|
| 1 | 4-Cl | H | H | 358-9 | 60.55 | 4.36 | 5.06 | 12.77 |
|   |   |   |   |   | 60.85 | 4.42 | 4.99 | 13.07 |
| 2 | 4-Cl | H | Na | >300 | 56.10 | 3.70 | 4.67 | 11.83 |
|   |   |   |   |   | 55.29 | 3.78 | 4.73 | 11.65 |
| 3 | H | H | H | 250-1 | 69.12 | 5.39 | 5.76 | — |
|   |   |   |   |   | 69.57 | 5.40 | 5.61 | — |
| 4 | H | H | Na | >300 | 63.39 | 4.56 | 5.28 | — |
|   |   |   |   |   | 61.54 | 4.78 | 5.18 | — |
| 5 | 4-CH₃ | H | H | 238-40 | 70.02 | 5.88 | 5.45 | — |
|   |   |   |   |   | 70.14 | 6.02 | 5.29 | — |
| 6 | 4-CH₃ | H | Na | >300 | 64.51 | 5.05 | 5.02 | — |
|   |   |   |   |   | 63.45 | 5.18 | 5.09 | — |
| 7 | 3,4-diCl | H | H | 276-7 | 53.87 | 3.55 | 4.49 | 22.72 |
|   |   |   |   |   | 54.02 | 3.54 | 4.32 | 22.68 |
| 8 | 3,4-diCl | H | Na | 296-7 | 50.32 | 3.02 | 4.19 | 21.22 |
|   |   |   |   |   | 45.25 | 3.17 | 4.05 | 21.40 |
| 9 | 4-F | H | H | 260-1 | 64.36 | 4.63 | 5.36 | 7.27 |
|   |   |   |   |   | 63.89 | 4.59 | 5.53 | 7.07 |
| 10 | 4-F | H | Na | >300 | 59.36 | 3.92 | 4.95 | 6.71 |
|   |   |   |   |   | 58.83 | 3.88 | 5.03 | 4.95 |
| 11 | 3-Cl | H | H | 254-5 | 60.55 | 4.36 | 5.04 | 12.77 |

TABLE I-continued

| 12 | 3-Cl | H | Na | >300 | 60.03 | 4.31 | 5.05 | 13.63 |
|---|---|---|---|---|---|---|---|---|
|   |   |   |   |   | 56.10 | 3.70 | 4.67 | 11.83 |
|   |   |   |   |   | 53.57 | 3.75 | 4.46 | 11.45 |
| 13 | 4-CH₃, 3-Cl | H | H | 247-51 | 61.75 | 4.84 | 4.80 | 12.16 |
|   |   |   |   |   | 61.61 | 4.88 | 5.27 | 12.24 |
| 14 | 4-CH₃, 3-Cl | H | Na | >300 | 54.29 | 4.56 | 4.22 | 10.66 |
|   |   |   |   |   | 54.88 | 4.23 | 4.39 | 11.05 |
| 15 | 4-OCH₃ | H | H | 219-21 | 65.92 | 5.53 | 5.13 | — |
|   |   |   |   |   | 65.52 | 5.39 | 5.18 | — |
| 16 | 4-OCH₃ | H | Na | 295-8 | — | — | — | — |
| 17 | 4-CF₃ | H | H | 230-2 | 57.88 | 3.89 | 4.50 | 18.31 |
|   |   |   |   |   | 58.31 | 3.93 | 4.66 | 18.04 |
| 18 | 4-CF₃ | H | Na | >300 | — | — | — | — |
| 19 | 4-Br | H | H | 244-6 | 52.19 | 3.76 | 4.35 | 24.81 |
|   |   |   |   |   | 52.67 | 3.85 | 4.60 | 24.84 |
| 20 | 4-Br | H | Na | >300 | — | — | — | — |
| 21 | 4-Cl naphthyl | H | H | 264-6 | 65.96 | 4.31 | 4.27 | 10.82 |
|   |   |   |   |   | 65.68 | 4.27 | 4.41 | 11.03 |
| 22 | 4-Cl naphthyl | H | Na | >300 | — | — | — | — |
| 23 | 4-Cl | Br | H | 243-6 | 47.14 | 3.11 | 3.93 | — |
|   |   |   |   |   | 47.65 | 3.13 | 4.29 | — |
| 24 | 4-Cl | Br | Na | >220 | — | — | — | — |
| 25 | 4-Br | Br | H | 248-50 | 41.92 | 2.77 | 3.49 | 39.85 |
|   |   |   |   |   | 42.06 | 2.72 | 3.91 | 40.33 |
| 26 | 4-Br | Br | Na | 290 | — | — | — | — |
| 27 | 4-Br | H | C₂H₅ | 129-30 | 54.87 | 4.61 | 4.00 | 22.82 |
|   |   |   |   |   | 54.97 | 4.69 | 3.98 | 23.33 |
| 28 | 4-I | H | H | 226-30 | 45.55 | 3.28 | 3.80 | 34.38 |
|   |   |   |   |   | 50.80 | 3.78 | 4.40 | 28.56 |
| 29 | 4-I | H | Na | >300 | — | — | — | — |

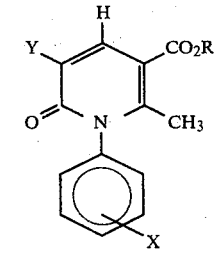

| 30 | 4-Cl | H | H | 271-73 | 59.21 | 3.82 | 5.31 | 13.45 |
|---|---|---|---|---|---|---|---|---|
|   |   |   |   |   | 59.17 | 3.76 | 5.71 | 13.49 |

EXAMPLE 1

Preparation of N-(4-chlorophenyl)-5-carboxy-4,6-dimethylpyrid-2-one (a) 4-Chloroaniline (48.4 g), p-toluene sulfonic acid (4.7 g) and ethyl isodehydacetate (65 g) are suspended in cumene (260 ml). The reaction mixture is brought to reflux, and water collected in a Dean-Stark trap. After 18 hours, the reaction mixture is cooled and washed with dilute hydrochloric acid to remove excess 4-chloroaniline. The cumene is then removed in vacuo, leaving the crude 5-carbethoxy-N-(4-chlorophenyl)-4,6-dimethylpyrid-2-one as a dark brown oil.

(b) The crude ester prepared in (a) above is suspended in a solution prepared by mixing methanol (500 ml), water (500 ml) and 50% aqueous sodium hydroxide (50 g). The suspension is refluxed for six hours. The solvent is then removed in vacuo and replaced with water (1000 ml). Insoluble material is filtered off and discarded. The clear aqueous layer is then acidified with hydrochloric acid and the resulting precipitate is filtered and dried, to yield (after recrystallization from acetone) 55 g of product, N-(4-chlorophenyl)-4,6-dimethylpyrid-2-one-5-carboxylic acid, having a melting point of 258°-9° (decomposition).

EXAMPLE 19

Preparation of
N-(4-bromophenyl)-5-carboxy-4,6-dimethylpyrid-2-one

Ethyl isodehydracetate (20 g 0.102 mole) and 4-bromoaniline (19.3 g, 0.112 mole are dissolved in 50% aqueous acetic acid (100 ml). The mixture is refluxed for 12 hours, the solvent removed, and the crude ester isolated as a brownish oil.

The crude ester isolated above is heated for 6 hours with 300 g 5% NaOH in 1:1 methanol/water. The mixture is cooled, diluted with water (100 ml) and filtered to remove insolubles. Some of the methanol is removed in vacuo, and an additional portion of water is added. The clear basic solution is then acidified and the resulting precipitate is filtered and dried. Recrystallization from acetonitrile provides pure N-(4-bromophenyl)-5-carboxy-4,6-dimethylpyrid-2-one (5.3 g, 16.1% yield) having a melting point of 244°–6° (dec.).

EXAMPLE 25

Preparation of
N-(4-bromophenyl)-3-bromo-5-carboxy-4,6-dimethylpyrid-2-one

Sodium N-(4-bromophenyl)-4,6-dimethylpyrid-2-one-5-carboxylate (285 g, 0.00828 mole) is dissolved in dry methanol (50 ml). Bromine (1.59 g, 0.00994 moles, 1.2 equivalents) is dissolved in methanol (50 ml) and slowly drop-added to the vigorously stirred salt solution over a period of 15 to 20 minutes. The solvent is then removed and the residue taken up in dilute base.

After filtering off the insoluble material, the clear basic aqueous solution is acidified with hydrochloric acid. The resulting precipitate is filtered and dried, and recrystallized from acetonitrile to yield N-(4-bromophenyl)-3-bromo-5-carboxy-4,6-dimethyl-pyrid-2-one (2.25 g, 67.8%) having a melting point of 248°–250°.

EXAMPLE 28

Preparation of
N-(4-iodophenyl)-5-carboxy-4,6-dimethylpyrid-2-one

Ethyl isodehydracetate (15 g, 0.075 mole) and 4-iodoaniline (19.05 gms, 0.0870 mole) are dissolved in 100 gms 50% aqueous acetic acid. The mixture is refluxed 6½ hrs, the solvent removed and the crude ester isolated as a black oil.

The crude ester isolated above is heated for 6 hours with 300 gms 5% NaOH in 1:1 methanol/water. The mixture is cooled, filtered to remove $H_2O$-insoluble material and the aqueous residue is acidified. The resulting acidic mixture is extracted with chloroform (2×200 mls). Removal of the solvent and recrystallization of the oil that remains from methylene chloride/ether yields the desired carboxylic acid (1.5 gms, 5%) having a melting point of 226°–30°.

EXAMPLE 30

Preparation of
N-(4-chlorophenyl)-5-carboxy-6-methylpyrid-2-one (a) Ethyl β-anilinocrotonate (23.9 g) is dissolved in dry benzene (200 ml) and placed in a flask under a nitrogen atmosphere. Acryloyl chloride (10 g) is dissolved in additional dry benzene (200 ml) and drop-added via a sidearm additional funnel over the course of 1½ hour. The reaction mixture is allowed to stand at about 25° for one hour, and then poured into water and extracted with methylene chloride. Evaporation of the solvent yields crude 5-carbethoxy-N-(4-chlorophenyl)-6-methyl-3,4-dihydropyrid-2-one (23.3 g) having a melting point of 124°–6° (from hexane/ether).

(b) The ester (15 g) prepared in (a) above is dissolved in chlorobenzene (500 ml). 2,3-Dichloro-5,6-dicyano-1,4-benzoquinone (DDQ) (23.2 g) is added and the mixture refluxed for 3 hours. The reaction mixture is then cooled, filtered and diluted with an equal volume of methylene chloride and washed exhaustively with dilute aqueous sodium bicarbonate. The solvent is removed in vacuo and the residue of crude product is recrystallized from hexane-ether to yield pure 5-carbethoxy-N-(4-chlorophenyl)-6-methylpyrid-2-one (8.3 g) having a melting point of 53°–4°.

(c) The pyridone (7.0 g) prepared in (b) above is suspended in 5% aqueous sodium hydroxide (200 ml). The mixture is heated on a steambath for one hour, cooled and acidified with aqueous hydrochloric acid to yield N-(4-chlorophenyl)-5-carboxy-6-methylpyrid-2-one (4.0 g) which, when recrystallized from acetonitrile has a melting point of 271°–3° with decomposition.

The compounds of the invention are particularly useful as chemical gametocides in cereal crops, such as wheat, barley, corn, rice, sorghum, millets, oats, rye and the like. When used as chemical gametocides, the compounds effectively induce a high degree of sterility in the treated plants, without causing a significant growth inhibition of the treated plants. The compounds of the invention also cause other plant growth regulatory responses, such as for example, inhibition of seed formation in undesirable monocot species for weed grass control, control of flowering, control of fruiting and inhibition of seed formation in non-cereal species, control of ripening, and other related growth regulatory responses.

When used as plant growth regulators, the compounds of the invention are applied in any amount which will be sufficient to effect the desired plant response without causing any undesirable or phytotoxic response. For example, when the compounds of the invention are used as chemical gametocides, they are generally applied to the plants to be treated at a rate of about 1/32 to about 20 pounds per acre and preferably about ⅛ to about 10 pounds per acre. The rate of application will vary depending on the plant species being treated, the compound being used for treatment, and related factors.

A preferred method of applying a compound of the invention as a plant growth regulator is by foliar application. When this method is employed, gametocidal activity is most effectively induced when the compound is applied prior to meiosis, and preferably after flower initiation. The compounds of the inventions may also be applied as a seed treatment by soaking the seed in a liquid formulation containing the active compound or by coating the seed with the compound. In seed treatment applications, the compounds of the invention will generally be applied at a rate of about ¼ to about 10 pounds per hundred weight of seed. The compounds of the invention can also be applied to the soil or, in rice crops, to the water surfaces.

The compounds of the invention can be used as plant growth regulators either individually or in mixtures. For example, they can be used in combination with other plant growth regulators, such as auxins, gibberellins, morphactins, ethylene-releasing agents such as ethephon, pyridones, cytokinins, maleic hydrazide, succinic acid 2,2-dimethylhydrazine, chloride and its salts, (2-chloroethyl) trimethylammonium chloride, triiodobenzoic acid, tributyl-2,4-dichlorobenzylphosphonium chloride, polymeric N-vinyl-2-oxazolidinones, tri(dimethylaminoethyl) phosphate and its salts, and N-dimethylamino-1,2,3,6-tetrahydrophthalamic acid and its salts, 2,3-dichloroisobutyric acid and its salts, 3-(4-chlorophenyl)-6-methoxy-s-triazine-2,4-(1H,3H)dione, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no significant detrimental effect on the soil, equipment, crops or agronomic environment. Mixtures of compounds of the invention may also be used in any of these formulations. Compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired suitable surfactants are incorporated.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethylsulfoxide, and the like. Mixtures of these solvents can also be used. The concentration of the solution can vary from about 2% to about 98% by weight with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent or surfactant which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% by weight and in flowable emulsion concentrates this can be as high as about 75%.

Wettable powders suitable for spraying can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent may generally constitute about 0.5% to about 3% by weight of the composition, and a wetting agent may generally constitute from about 0.1% to about 5% by weight of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% by weight use concentration.

Granular formulations can be prepared by imgrenating a solid such as granular fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to about 15% by weight of the granular formulation.

Salts of the compounds of the invention can be formulated and applied as aqueous solutions. The salt will typically comprise about 0.05 to about 50% by weight, preferably about 0.1% to about 10%, of the solution. These compositions can also be further diluted with water if desired prior to actual application. In some applications, the activity of these compositions can be enhanced by incorporating into the composition an adjuvant such as glycerin, methylethylcellulose, hydroxyethylcellulose, polyoxyethylenesorbitan monooleate, polypropylene glycol, polyacrylic acid, polyethylene sodium malate, polyethylene oxide, or the like. The adjuvant will generally comprise about 0.1 to about 5% by weight, preferably about 0.5 to about 2%, of the composition. Such compositions can also optionally include an agronomically-acceptable surfactant.

The compounds of the invention can be applied as sprays by methods commonly employed, such as conventional hydraulic sprays, aerial sprays, and dusts. For low-volume applictions a solution of the compound is usually used. The dilution and volume of application will usually depend upon such factors as the type of equipment employed, the method of application, the area to be treated and the type and stage of development of the crop being treated.

The following examples will further illustrate the growth regulatory activity of the compounds of the invention but are not intended to limit the invention in any way.

EXAMPLE 31

Chemical Gametocidal Activity

The following procedures are used to evaluate the activity of the compounds of the invention as chemical gametocides in cereals An awned variety (Fielder) and an awnless variety (Mayo-64) of spring wheat are planted at the rate of 6 to 8 seeds per 6" pot containing a sterile medium of 3 parts soil and 1 part humus. The plants are grown under short-day (9 hour) conditions for the first 4 weeks to obtain good vegetative growth before flower initiation. The plants are then moved to long-day (16 hour) conditions which are provided by high intensity lights in the greenhouse. The plants are fertilized at 2, 4, and 8 weeks after planting with a water soluble fertilizer (16-25-16) at the rate of 1 tsp/gal of water, and are frequently sprayed with isotox for aphid control and dusted with sulfur for powdery mildew control.

Test compounds are foliarly applied to the awned female plants when these plants reach the flag leaf emergence stage (stage 8 on Feekes' scale*). All compounds are applied in a carrier volume of 50 gal/A containing a surfactant, such as Triton® X-100, at the rate of 2 oz/50 gal.

*W. Feekes, Vers. 17 Tech. Tarwe Comm. Groningen, pp 560–561, 1941.

After spike emergence but before anthesis, 4 to 6 spikes per pot are bagged to prevent outcrossing. At the first signs of flower opening, two spikes per pot are cross pollinated, using the approach method, with the awnless male parent. As soon as the seeds became plainly visible, spike length is measured and seeds per spikelet counted in both bagged and crossed spikes. Male sterility is then calculated as percent inhibition of seed set in bagged spikes of treated plants. After maturity the seed on crossed spikes can be planted for determination of percent hybridization.

Percent sterility is calculated from the following formula:

$$\% \text{ Sterility} = \frac{S_c - S_t}{S_c} \times 100$$

$S_c$ = seeds/spikelet in bagged spikes of control plants
$S_t$ = seeds/spikelet in bagged spikes of treated plants Table II summarizes typical results obtained in the evaluation of compounds of the invention. A dash indicates that no test at the indicated rate was made.

TABLE II

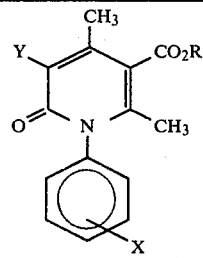

| | | | Rate (lb/A) | | | | | | |
|---|---|---|---|---|---|---|---|---|---|
| | | | % Sterility | | | | | | |
| X | Y | R | 8 | 4 | 2 | 1 | ½ | ¼ | ⅛ |
| 4-Cl | H | H | 100 | 100 | 100 | 96 | — | — | — |
| 4-Cl | H | Na | 100 | 100 | 100 | 100 | 92 | 52 | — |
| H | H | H | 22 | 0 | 4 | 6 | — | — | — |
| H | H | Na | 46 | 0 | 13 | 8 | — | — | — |
| 4-CH₃ | H | H | 21 | 0 | 0 | 14 | 13 | 12 | 2 |
| 4-CH₃ | H | Na | 0 | 0 | 0 | 14 | 11 | 2 | 3 |
| 3,4-diCl | H | H | 98 | 93 | 80 | 12 | 20 | 16 | 12 |
| 3,4-diCl | H | Na | 96 | 91 | 33 | 22 | 25 | 21 | 4 |
| 4-F | H | H | 0 | 0 | 0 | 9 | 0 | 24 | 13 |
| 4-F | H | Na | 0 | 0 | 0 | 2 | 7 | 18 | 15 |
| 3-Cl | H | H | 4 | 0 | 0 | 0 | 3 | 3 | 2 |
| 3-Cl | H | Na | 0 | 2 | 0 | — | — | — | — |
| 4-CH₃, 3-Cl | H | H | 6 | 4 | 0 | 19 | 0 | — | — |
| 4-CH₃, 3-Cl | H | Na | 0 | 2 | 1 | 0 | 1 | 6 | — |
| 4-OCH₃ | H | H | 56 | 18 | 2 | 9 | — | — | — |
| 4-OCH₃ | H | Na | 54 | 31 | 0 | 3 | — | — | — |
| 4-CF₃ | H | H | 15 | 3 | — | — | — | — | — |
| 4-CF₃ | H | Na | 0 | 3 | 0 | 0 | 1 | — | — |
| 4-Br | H | H | 100 | 100 | 100 | — | — | — | — |
| 4-Br | H | Na | 100 | 100 | 100 | 100 | 100 | 100 | 100 |
| 4-Cl naphthyl | H | H | 2 | — | — | — | — | — | — |
| 4-Cl naphthyl | H | Na | 14 | 4 | 0 | 0 | — | — | — |
| 4-Cl | Br | H | 9 | 7 | 9 | 16 | 13 | — | — |
| 4-Cl | Br | Na | 15 | 13 | 13 | 20 | 13 | — | — |
| 4-Br | Br | H | — | — | — | — | — | — | — |
| 4-Br | Br | Na | 100 | 99 | 89 | 43 | 25 | — | — |
| 4-Br | H | C₂H₅ | 100 | — | 100 | — | 100 | — | 100 |
| 4-I | H | Na | — | — | — | — | 100 | 100 | 100 |

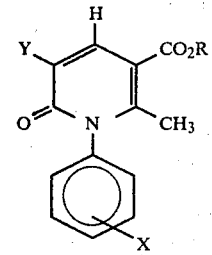

| | | | | | | | |
|---|---|---|---|---|---|---|---|
| 4-Cl | H | H | 100 | 88 | 49 | 19 | — | — | — |
| 4-Cl | H | Na | 100 | 100 | 90 | 39 | — | — | — |

The data in Table III below demonstrates the male sterilant activity of the compounds of this invention on small grain cereal in addition to wheat. In this test the compounds were applied foliarly at growth stage 7 (Feeke's Scale) to a spring type triticale and rice and a winter type rye all grown under greenhouse conditions. Incomplete vernilization on rye and a long season nature of rice caused their growth stages to be variable at treatment time. This data demonstrates that the N-halogen-substituted phenylpyrid-2-one sodium salt possesses chemical male sterilant activity on various small grain cereals in addition to wheat.

TABLE III

N-(4-Bromophenyl)-4,6-dimethyl-5-carboxypyrid-2-one sodium salt

| | % Sterility/Rate lb/A | | | | | |
|---|---|---|---|---|---|---|
| Crop | 4 | 2 | 1 | ½ | ¼ | ⅛ |
| Triticale (Setter) | 100 | 100 | 100 | 98 | — | — |
| Rye (Puma)[a] | 100 | 99 | 93 | 100 | — | — |
| Rice (Bella Patna)[b] | 0 | 8 | 0 | 15 | — | 6 |

[a]The growth stage in rye was variable at treatment time causing data to be inconsistent, however, male sterilant activity was present.
[b]The growth stage in rice was variable at treatment time causing data to be inconsistent, however, male sterilant activity was indicated.

Table IV below demonstrates that the N-halogen-substituted phenylpyrid-2-ones of this invention possess unexpected male sterility accompanied by plant injury and only slight spike inhibition at high dosage levels as compared to the unsubstituted N-unsubstituted-phenyl-pyrid-2-one compound disclosed in the literature by Prey et al. in "Chemical Abstracts" vol. 56, column 15469, (1962) which possesses no activity. This data was obtained from a side-by-side comparative test following the test procedure utilized in Example 31 above except that the chemical agents were applied at stage 7 on the Feeke's scale.

TABLE IV

| Structure | Rate lbs/A | Percent Spike Inhibition | Percent Sterility | Injury Rank |
|---|---|---|---|---|
| Cl—⟨phenyl⟩—N(CH₃,CO₂Na,CH₃)=O | 1 | 0 | 77 | 0 |
|  | 2 | 0 | 86 | 0 |
|  | 4 | 1 | 100 | 0 |
|  | 8 | 7 | 100 | 0 |
| Cl—⟨phenyl⟩—N(CH₃,CO₂Na)=O | 1 | 0 | 3 | 0 |
|  | 2 | 0 | 1 | 0 |
|  | 4 | 0 | 55 | 0 |
|  | 8 | 3 | 100 | 0 |
| Cl—⟨phenyl(Cl)⟩—N(CH₃,CO₂Na,CH₃)=O | 1 | 0 | 1 | 0 |
|  | 2 | 0 | 45 | 0 |
|  | 4 | 0 | 85 | 0 |
|  | 8 | 0 | 82 | 0 |
| CH₃O—⟨phenyl⟩—N(CH₃,CO₂Na,CH₃)=O | 1 | 0 | 0 | 0 |
|  | 2 | 0 | 0 | 0 |
|  | 4 | 0 | 2 | 0 |
|  | 8 | 0 | 1 | 0 |
| ⟨phenyl⟩—N(CO₂Na)=O | 1 | 0 | 0 | 0 |
|  | 2 | 0 | 0 | 0 |
|  | 4 | 0 | 0 | 0 |
|  | 8 | 0 | 1 | 0 |

Table V below demonstrates that the N-halogen-substituted phenyl-5-carboxypyrid-2-ones of this invention possess unexpectedly good male sterility activity and little if any spike inhibition activity as compared to the N-halogen substituted phenyl-3-carboxy-pyrid-2-ones disclosed in the literature by Seidel et al. in U.S. Pat. No. 3,576,814 granted Apr. 27, 1971.

The procedure for measuring percent male sterility is that disclosed in the present specification as Example 31. The procedure for measuring percent female fertility and percent spike inhibition is as follows.

The spring wheat is planted at the rate of six to eight seeds per six inch pot containing a sterile medium of three part soil and one part humus. The plants are grown under short-day (nine hour) conditions for the first four weeks to obtain good vegetative growth before flower initiation. The flowers are then moved to a long-day (sixteen hour) conditions which are provided by high intensity lights in the greenhouse. The plants are fertilized at 2,4 and 8 weeks after planting with a water soluble fertilizer (16-25-16) at the rate of one teaspoon per gallon of water, and are frequently sprayed with an appropriate insecticide, such as ISOTOX ®, for aphid control and dusted with sulfur for powdery mildew control (test compounds are foliarly applied to the female plants when these plants reach the flag leaf emergence state (stage 8 on Feekes' scale). All compounds are applied in a carrier volume of 58 gallons per acre containing a surfactant, such as TRITON ® X-100, at the rate of 2 ounces per 50 gallons.

After spike emergence but before anthesis, four to six spikes per pot are bagged to prevent outcrossing. At the first signs of flower opening, two spikes per pot are cross pollinated, using the approach method, with the awnless male parent. As soon as the seeds become plainly visible, spike length is measured and seeds per spikelet counted on both bagged and crossed spikes. Female fertility in cross spikes can be calculated as percent of control seed set. The percent fertility and percent spike length inhibition are calculated from the following formulas:

$$\% \text{ fertility} = \frac{Ft}{Fc} \times 100 \quad (A)$$

Ft = seeds/spikelets in approached crossed spikes of treated plants
Fc = seeds/spikelets in unbagged spikes of control plants $$\% \text{ spike inhibition} = \frac{Hc - Ht}{Hc} \times 100$$

Hc = spike length of control plants
Ht = spike length of treated plants

This data demonstrates that the sodium salt of the N-(3',4'-dichlorophenyl)-4,6-dimethyl-3-carboxy-pyrid-2-one disclosed in the Seidel patent U.S. Pat. No. 3,567,814 as Example 13 as the free acid, is a non-selective plant growth regulator in that it not only possesses a high degree of male sterility activity but also a high degree of spike inhibition which is an undesirable side effect for the production of hybrid seed. Whereas, the compounds which correspond to Example No. 2 and Example No. 20 of the present specification both of which are 5-carboxypyridones possess good male sterility activity and little if any spike inhibition activity. Therefore the 5-carboxypyridone compounds of this invention are unexpectedly superior for use in hybrid seed programs as compared to the Seidel compounds.

TABLE V

| | Cl—⟨phenyl(Cl)⟩—N—pyridone(CH₃, CH₃, CO₂Na)=O | | | | Cl—⟨phenyl(Cl)⟩—N—pyridone(CO₂Na, CH₃, CH₃)=O | | | |
|---|---|---|---|---|---|---|---|---|
| Rate (lb/A) | 1 | ½ | ¼ | ⅛ | 1 | ½ | ¼ | ⅛ |
| % Sterility | 22 | 25 | 21 | 4 | 100 | 100 | 90 | 32 |
| % Inhibition | 7 | 8 | 1 | 9 | 45 | 40 | 34 | 29 |
| % Fertility | 87 | —a | — | — | — | 7 | 22 | 56 | a means not tested.

It should be understood that changes and variations may be made without departing from the spirit and scope of the invention as defined by the appended claims.

I claim:

1. The compound having the formula

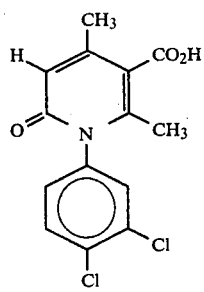

and the agronomically acceptable salts or carb($C_1$–$C_4$)alkoxy esters thereof.

2. The compound having the formula

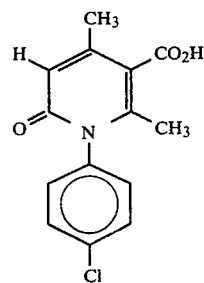

and the agronomically acceptable salts or carb($C_1$–$C_4$)alkoxy esters thereof.

3. The compound having the formula

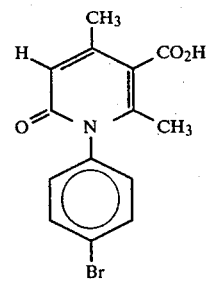

and the agronomically acceptable salts or carb($C_1$–$C_4$)alkoxy esters thereof.

4. The compound having the formula

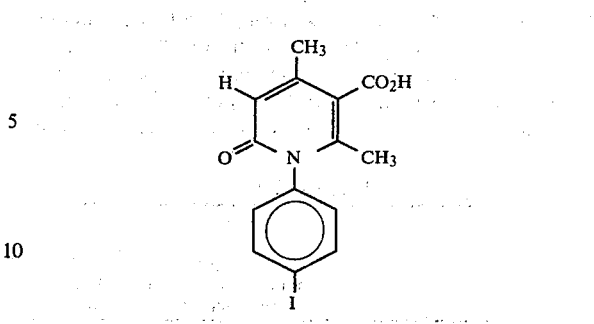

and the agronomically acceptable salts or carb($C_1$–$C_4$)alkoxy esters thereof.

5. The compound having the formula

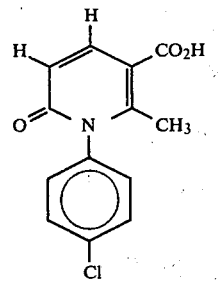

and the agronomically acceptable salts or carb($C_1$–$C_4$)alkoxy esters thereof.

6. A compound of the formula

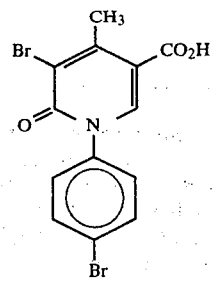

and the agronomically acceptable salts or carb($C_1$–$C_4$)alkoxy esters thereof.

7. A growth regulant composition which comprises an effective amount of a compound of claims 1, 2, 3, 4, 5 or 6 and an agronomically-acceptable carrier.

8. A method of inhibiting plant growth which comprises applying to the plant, the plant seeds, or the plant habitat an effective amount of a compound of claims 1, 2, 3, 4, 5 or 6.

9. The method of claim 1, 2, 3, 4, 5 or 6 wherein the plant is a cereal grain.

10. The method of claims 1, 2, 3, 4, 5 or 6 wherein the compound is applied to the plant prior to meiosis in an amount effective to produce male sterility in the plant.

* * * * *

UNITED STATES PATENT AND TRADEMARK OFFICE
CERTIFICATE OF CORRECTION

PATENT NO. : 4,238,220

DATED : December 9, 1980

INVENTOR(S) : Glenn R. Carlson

It is certified that error appears in the above—identified patent and that said Letters Patent is hereby corrected as shown below:

Column 3, line 39, "N-((4-bromophenyl)-5-carboxy-6-methylpyrid-2-one" should read -- N-(4-bromophenyl)-5-carboxy-6-methylpyrid-2-one --.

Column 9, line 1, "2,2-dimethylhydrazine" should read -- 2,2-dimethylhydrazide --.

Column 16, lines 34-44, the formula of claim 6 reading

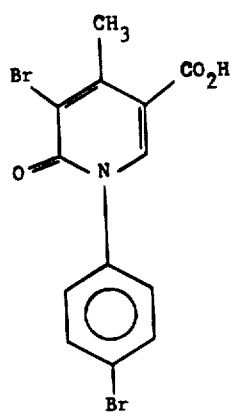   should read   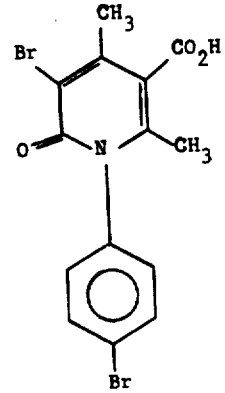

Signed and Sealed this

Fifteenth Day of November 1983

[SEAL]

Attest:

GERALD J. MOSSINGHOFF

Attesting Officer    Commissioner of Patents and Trademarks